US009790460B2

(12) United States Patent
Goetheer et al.

(10) Patent No.: US 9,790,460 B2
(45) Date of Patent: Oct. 17, 2017

(54) ENZYME PROMOTED CO₂ CAPTURE INTEGRATED WITH ALGAE PRODUCTION AND APPARATUS THEREFOR

(75) Inventors: Earl Lawrence Vincent Goetheer, Delft (NL); Peter Geerdink, Delft (NL); Ikenna Sunday Ngene, Delft (NL); Leo Jacques Pierre Van Den Broeke, Delft (NL)

(73) Assignee: NEDERLANDSE ORGANISATIE VOOR TOEGEPAST-NATUURWETENSCHAPPELUK ONDERZOEK TNO, Delft (NL)

( * ) Notice: Subject to any disclaimer, the term of this patent is extended or adjusted under 35 U.S.C. 154(b) by 488 days.

(21) Appl. No.: 14/238,224

(22) PCT Filed: Aug. 10, 2012

(86) PCT No.: PCT/NL2012/050557
§ 371 (c)(1),
(2), (4) Date: Jun. 4, 2014

(87) PCT Pub. No.: WO2013/022348
PCT Pub. Date: Feb. 14, 2013

(65) Prior Publication Data
US 2014/0295531 A1    Oct. 2, 2014

(30) Foreign Application Priority Data
Aug. 11, 2011 (EP) .................... 11177302

(51) Int. Cl.
| C12M 1/00 | (2006.01) |
| C12N 1/02 | (2006.01) |
| C12N 1/12 | (2006.01) |
| B01D 53/78 | (2006.01) |
| C12M 1/40 | (2006.01) |
| B01D 53/75 | (2006.01) |
| B01D 53/84 | (2006.01) |
| C12P 19/02 | (2006.01) |
| C12P 3/00 | (2006.01) |
| C12P 7/64 | (2006.01) |
| B01D 53/86 | (2006.01) |

(52) U.S. Cl.
CPC .............. *C12M 29/20* (2013.01); *B01D 53/75* (2013.01); *B01D 53/78* (2013.01); *B01D 53/84* (2013.01); *C12M 21/02* (2013.01); *C12M 21/18* (2013.01); *C12M 23/18* (2013.01); *C12M 43/00* (2013.01); *C12N 1/02* (2013.01); *C12N 1/12* (2013.01); *C12P 3/00* (2013.01); *C12P 7/6409* (2013.01); *C12P 7/649* (2013.01); *C12P 19/02* (2013.01); *B01D 53/86* (2013.01); *B01D 2251/95* (2013.01); *B01D 2252/103* (2013.01); *B01D 2255/70* (2013.01); *B01D 2255/804* (2013.01); *B01D 2257/504* (2013.01); *Y02C 10/02* (2013.01); *Y02C 10/04* (2013.01); *Y02E 50/13* (2013.01); *Y02P 20/134* (2015.11); *Y02P 20/152* (2015.11); *Y02P 20/59* (2015.11)

(58) Field of Classification Search
CPC ................ B01D 2255/804; B01D 53/84; F23J 2215/50; F23J 2219/40; C12N 9/88; C12Y 102/01001
USPC ......................... 422/168, 187; 435/232, 266
IPC .............. B01D 56/62,53/84; B01J 8/00; C12N 9/88
See application file for complete search history.

(56) References Cited

U.S. PATENT DOCUMENTS
2010/0086983 A1* 4/2010 Gellett ............... B01D 53/1475
435/168

FOREIGN PATENT DOCUMENTS
| WO | 2006/108532 A1 | 10/2006 |
| WO | 2008/107896 A2 | 9/2008 |
| WO | 2010/151787 A1 | 12/2010 |

OTHER PUBLICATIONS

Minic et al. 2011. The Biological Deep Sea Hydrothermal Vent as a Model to Study Carbon Dioxide Capturing Enzymes. Marine Drugs, vol. 9, pp. 719-738.*
Gong et al. 2011. Biodiesel production with microalgae as feedstock: from strains to biodiesel. Biotechnology Letters, vol. 33:1269-84.*
Ramanan, R., et al: "Enhanced algal CO2 sequestration through calcite deposition by *Chlorella* sp. and *Spirulina platensis* in a mini-raceway pond", Bioresource Technology, Elsevier BV, GB, vol. 101, No. 8, Apr. 1, 2010 (Apr. 1, 2010), pp. 2616-2622, ISSN: 0960-8524, [retrieved Nov. 25, 2009].
Skjanes, et al: "BioCO2—A multidisciplinary, biological approach using solar energy to capture CO2 while producing H2 and high value products II", Biomolecular Engineering, Elsevier, New York, NY, US, vol. 24. No. 4, Sep. 16, 2007 (Sep. 16, 2007), pp. 405-413, ISSN: 1389-0344.
Favre, N., et al: "Biocatalytic capture of CO2 with carbonic anhyrdase and its transformation to solid carbonate", Journal of Molecular Catalysis. B. Enzymatic, Elsevier, Amersterdam, NL, vol. 60, No. 3-4, Oct. 1, 2009 (Oct. 1, 2009), pp. 163-170, ISSN: 1381-1177, [retrieved on May 6, 2009].
Mitra, Mautusi, et al: "The carbonic anhydrase gene families of *Chlamydomonas reinhardtii*", Canadian Journal of Botany / Journal Canadien De Botanique. National Research Council, Ottawa, CA, vol. 83, No. 7, Jul. 1, 2005 (Jul. 1, 2005), pp. 780-795.
Yang, H., et al: "Progress in carbon dioxide separation and capture: A review", A Journal of Environmental Sciences, vol. 20, No. 1, Jan. 1, 2008 (Jan. 1, 2008), pp. 14-27, [retrieved on Jan. 1, 2008].
Pruvost, J., et al: "Investigation of biomass and lipids production with Neochloris oleoabundans in photobioreactor", Bioresource Technology, Elsevier BV, GB, vo 1 100, No. 23, Dec. 1, 2009 (Dec. 1, 2009), pp. 5988-5995.

* cited by examiner

*Primary Examiner* — Debbie K Ware
*Assistant Examiner* — Kailash C Srivastava
(74) *Attorney, Agent, or Firm* — Lucas & Mercanti, LLP

(57) ABSTRACT

The disclosure relates to the field of reduction of $CO_2$ emission, more in particular to $CO_2$ capture and conversion. The disclosure further relates to the culturing of algae and an apparatus for use thereof. One object of the disclosure is to provide an alternative method for capturing and conversion of $CO_2$ from a gaseous stream.

19 Claims, 2 Drawing Sheets

ENZYME PROMOTED CO$_2$ CAPTURE INTEGRATED WITH ALGAE PRODUCTION AND APPARATUS THEREFOR

CROSS-REFERENCE TO RELATED APPLICATIONS

This application is a 371 of PCT/NL2012/050557, filed Aug. 10, 2012, which claims the benefit of European Patent Application No. 11177302.4, filed Aug. 11, 2011, the contents of each of which are incorporated herein by reference.

FIELD OF THE INVENTION

The invention relates to the field of reduction of CO$_2$ emission, more in particular to CO$_2$ capture and conversion. The invention further relates to the culturing of algae.

BACKGROUND OF THE INVENTION

The continued dependence on fossil fuels for energy production and the environmental effects of combustion of such fuels is commonly associated with the increasing climate change observed globally. The combustion of such fuels produces carbon dioxide (CO$_2$), a so-called greenhouse gas, which was previously generally released into the atmosphere. Because of the environmental effects of greenhouse gases, resulting for instance in global warming, there is ongoing research into the reduction of emission of CO$_2$ into the atmosphere. One method for reducing the emission of CO$_2$ into the atmosphere is for instance the capturing and storage of CO$_2$. The classical method used in CO$_2$ capture is reactive absorption followed by thermal regeneration of the absorbent liquid (Figueroa et al., *International Journal of Greenhouse Gas Control* 2008, 2(1), 9-20). Amines used to capture CO$_2$ from gaseous streams react to form water soluble compounds, which degrade on heating to release the CO$_2$. Monoethanolamine (MEA) is a regularly used base for the capture of CO$_2$, with efforts being put into developing other possibilities. However, the high energy input used for regenerating the absorbent liquid makes this method less favourable. Aside from this method, there is continuous work being done on newer technologies for the capture of CO$_2$ like use of gas membrane contactors (Powell et al., *Journal of Membrane Science* 2006, 279(1-2), 1-49), chilled ammonia process (Darde et al., *International Journal of Greenhouse Gas Control* 2010, 4(2), 131-136), formation of carbonates (Favre et al., *Journal of Molecular Catalysis B: Enzymatic* 2009, 60(3-4), 163-170), and use of ionic liquids (Hasib-ur-Rahman et al., *Chemical Engineering and Processing: Process Intensification* 2010, 49(4), 313-322).

However, after the capture of CO$_2$, there is still need to sequester or use the CO$_2$, in other words to keep it away from the atmosphere. Before the present invention, the capture and storage of CO$_2$, with sequestration in geologic forms has attracted attention (Figueroa et al., *International Journal of Greenhouse Gas Control* 2008, 2(1), 9-20). Also methods of converting the captured gas into methane, concrete and even in the use of sugar production have been explored by others.

WO-A-2010/151787 discloses CO$_2$ absorption by a carbonic anhydrase solution and using the resuling bicarbonate ions to facilitate growth of algae. However this document does not disclose separation of the rich absorbent liquid into two fractions, one of the fractions having a higher enzyme concentration than the other.

Ramanan et al. (*Bioresource Technology* 2010, 101, 2616-2622) disclose CO$_2$ sequestration using *Chlorella* sp. and *Spirulina platensis* algae. This document, too, does not disclose separation of the rich absorption liquid into two fractions, one of the fractions having a higher enzyme concentration than the other. Additionally, Ramanan et al. are silent as to recycling.

SUMMARY OF THE INVENTION

One objective of the present invention is to provide an alternative method for capturing and conversion of CO$_2$ from a gaseous stream.

In order to achieve said object, the present invention combines the enzyme catalysed CO$_2$ capture with algal growth. The combination of the two has advantages over methods known in the art. One advantage is for instance, that regeneration of the absorbent liquid does not require (high) energy input, as the regeneration is done by algae, preferably using solar energy (sunlight).

In a first embodiment, therefore, the invention provides a method for decreasing the amount of carbon dioxide (CO$_2$) in a gaseous stream, the method comprising the steps of
(1) contacting a gaseous stream comprising CO$_2$ with a first absorbent liquid stream comprising an enzyme capable of converting liquid-absorbed CO$_2$ into a more liquid-soluble inorganic carbon,
(2) allowing the CO$_2$ to be absorbed by said first absorbent liquid and allowing the liquid-absorbed CO$_2$ to be converted into said more soluble inorganic carbon,
(3) separating the first liquid stream comprising both the enzyme and the dissolved inorganic carbon into a second and a third liquid stream, wherein
(4) said second liquid stream comprises, relative to said third liquid stream, a higher concentration of the enzyme,
(5) recycling said enzyme by supplying the enzyme in said second liquid stream back, together with a portion of the absorbent liquid, to be contacted with the gaseous stream in method step (1),
(6) contacting said third liquid stream with a microorganism, preferably an alga, capable of converting liquid-solubilised inorganic carbon into oxygen and/or biomass and/or other algal products,
(7) allowing the conversion of the liquid-soluble inorganic carbon by said microorganism, thereby regenerating the absorbent liquid,
(8) recycling the regenerated absorbent liquid to be contacted with the gaseous stream in method step (1), preferably by first combining the regenerated absorbent liquid with the recycled enzyme of step (5).

The use of biological systems for the conversion of CO$_2$ has already been explored, however, until the present invention not in combination with catalysed CO$_2$ capture. It has been observed that algae, for instance, are suitable for converting CO$_2$ into water and oxygen, at least under laboratory scale conditions.

Algae are simple photosynthetic life forms which are able to directly convert CO$_2$ into energy. Algae are a potential source of biomass and fine chemicals, with efforts underway to modify algae for the production of bio-fuels. The direct use of algae in removal of CO$_2$ from gas streams has therefore generated some interest (Skjånes et al., *Biomolecular Engineering* 2007, 24(4), 405-413). However, work still needs to be done on the introduction of CO$_2$ into these algal ponds, considering the fact that direct injection of the exhaust gas into the ponds requires large surface areas and also results in inefficient capture of the contained CO$_2$. The $CO_2$ production in a coal-fired 500 MW power plant is well over 2.5 million ton of $CO_2$ per year. For direct injection into an algae pond, an open pond in the order of 5-10 km² of area is required. Typically, the land mass needed for algal ponds restricts the use of the captured $CO_2$ in algal growth.

DETAILED DESCRIPTION OF THE INVENTION

Figure 1:
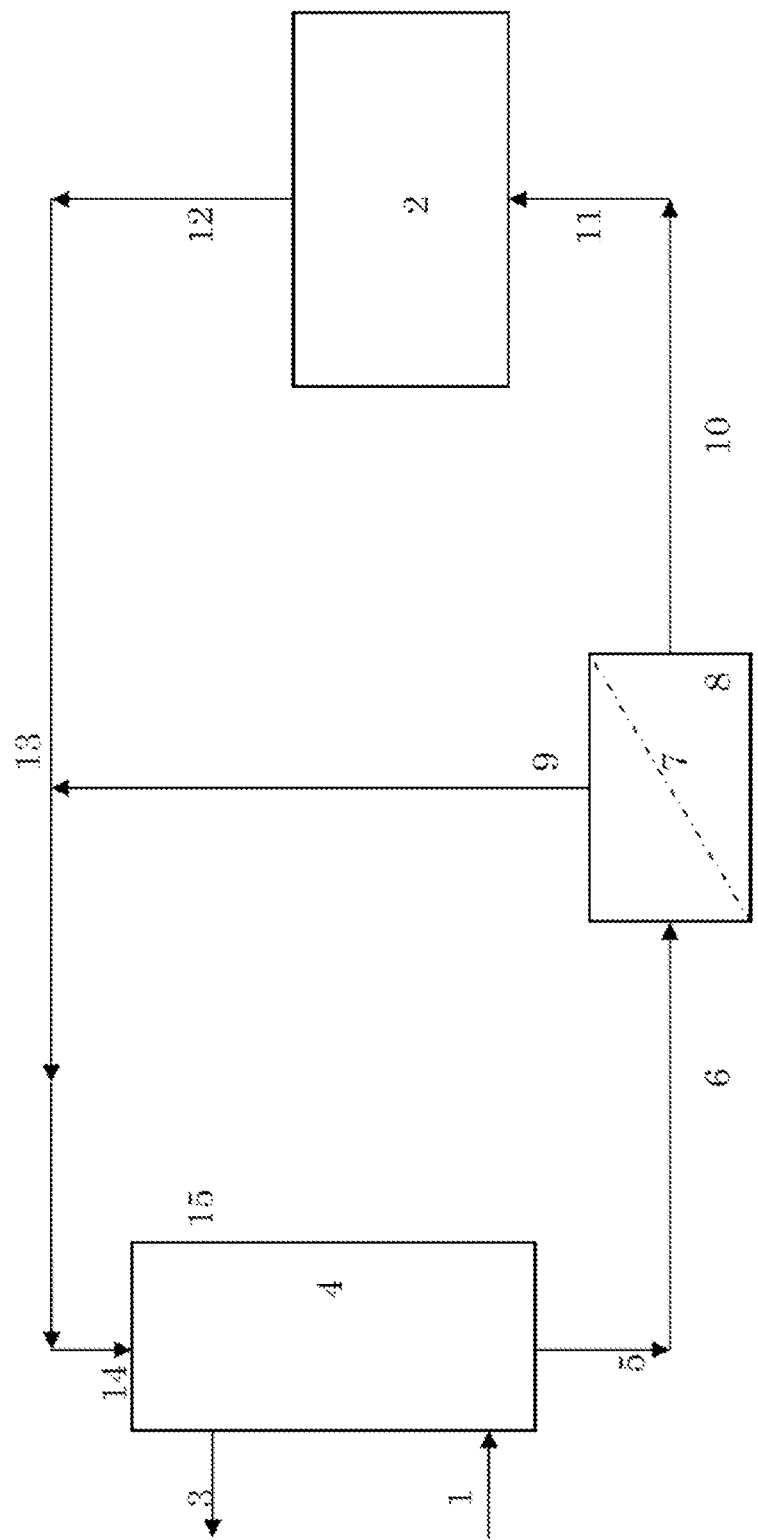
FIG. 1: Schematic illustration of an apparatus according to the invention for integration of the capture of $CO_2$ with direct consumption/regeneration

The present invention provides the insight that by combining catalytic conversion of $CO_2$ into a soluble organic carbon and conversion of the soluble organic carbon by algae, smaller algae ponds can be used to convert the majority of $CO_2$ produced by a power plant. Considering that the $CO_2$ is introduced into the pond in the dissolved form, this directly improves the efficiency of $CO_2$ uptake by the algae compared to direct injection of $CO_2$ whereby part of this is lost. This enhanced efficiency of $CO_2$ delivery can result in a reduction in pond specific surface area by up to 1.5-2 times.

Any gaseous stream comprising $CO_2$ can be used in a method according to the invention. In a preferred embodiment, the gaseous stream is a $CO_2$ rich gaseous stream, preferably flue gas. Use of flue gas as a $CO_2$ rich gaseous stream in a method according to the invention has the advantage that reduction of $CO_2$ emission by (coal-fired) power plants is combined with growth of algae. Reduction of $CO_2$ emission is important, because as a greenhouse gas, $CO_2$ is held responsible for global climate changes. As described further below, the thereby produced algae have utility in a multitude of applications.

Catalytic conversion of $CO_2$ can be achieved by several methods known in the art. Some of the methods include the use of photocatalysis, mixed amine systems whereby one acts more as a promoter for the second amine and iron catalysts for the production of hydrocarbons and polymers. It is however preferred that the catalyst used in a method according to the invention is an enzyme, preferably carbonic anhydrase.

Carbonic anhydrase enzymes (also referred to as carbonate anhydrase enzymes; EC 4.2.1.1) are enzymes capable of catalysing the hydration of $CO_2$ in aqueous liquids and are present in biological systems. One molecule of carbonic anhydrase can hydrate approximately 36 000 000 molecules of carbon dioxide in a period of sixty seconds. Carbonic anhydride enzymes are present in virtually all animals and are not only able to catalyse the hydration of $CO_2$ into bicarbonate, but also the reverse reaction, i.e. dehydration of bicarbonate. Carbonic anhydrase is one of the fastest enzymes known with a high turnover rate (Davy, *Energy Procedia* 2009, 1(1), 885-892) and the enzyme is robust which enables usage under industrial conditions. For mammalian carbonic anhydrase, there are at least 14 isoforms known. These mammalian carbonic anhydrase enzymes are divided into four broad subgroups depending on the tissue or cellular compartment location (e.g., cytosolic, mitochondrial, secreted, and membrane-associated). The carbonic anhydrase known to have the fastest turnover rate is carbonic anhydrase II. Carbonic anhydrase IV is known to have particularly high temperature stability and this stability is believed to stem from the two disulfide linkages in the enzyme. Also analogues of carbonic anhydrase enzymes are capable of converting liquid-absorbed $CO_2$ into a more liquid-soluble inorganic carbon.

These characteristics of carbonic anhydrase make it attractive for use in the capture of $CO_2$ from exhaust gas streams (Favre et al., *Journal of Molecular Catalysis B: Enzymatic* 2009, 60(3-4), 163-170, and Dilmore et al., *International Journal of Greenhouse Gas Control* 2009, 3(4), 401-410). Using carbonic anhydrase, work has been done on converting the $CO_2$ from these exhaust gas streams into solid carbonate forms which can further be utilised.

In a preferred embodiment, therefore, a method for decreasing the amount of carbon dioxide ($CO_2$) in a gaseous stream according to the invention is provided, wherein said enzyme is carbonic anhydrase or an analogue thereof.

Although a combination of carbonic anhydrase and conversion into bicarbonate has been documented before (Favre et al., *Journal of Molecular Catalysis B: Enzymatic* 2009, 60(3-4), 163-170), the present invention uses an enzyme, such as carbonic anhydrase or an analogue thereof for the formation of bicarbonate with direct application into an algae pond. This advantageous combination of an enzyme for converting $CO_2$ into bicarbonate and conversion of bicarbonate by algae has not been used before. The invention now provides the insight that combining enzymatic conversion of $CO_2$, preferably by carbonic anhydrase or an analogue thereof, and conversion of the resulting soluble inorganic carbon by algae has enormous advantages, especially when combined with additional features, such as recycling of the enzyme and recycling of the liquid capable of absorbing the $CO_2$ from the gaseous stream. These aspects will be explained in more detail further below.

In a preferred embodiment an enzyme, preferably carbonic anhydrase or analogue thereof, is used to hydrate $CO_2$, resulting in the formation of a bicarbonate (Equation 1), which is preferably directly fed into the algal pond after a separation step.

$$CO_3^{2-} + CO_2 + H_2O \leftrightarrow 2\ HCO_3^{-} \qquad \text{Equation 1}$$

The separation step serves to reintroduce the enzyme into the absorbing unit without first passing the enzyme into the algae pond or bioreactor. In this way, the enzyme can be reused without substantial losses, which would occur if the enzyme would be fed with the absorbent liquid into the algae pond. In a method of the invention, the absorbent liquid comprising the bicarbonate, fed into the algae pond is thus preferably essentially devoid of the enzyme used for conversion. The algae are capable of using the bicarbonate from the absorbent liquid to produce glucose biomass according to Equation 2. The algae can also directly use the $CO_2$ in the production of other algal products such as oils.

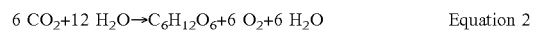

$$6\ CO_2 + 12\ H_2O \rightarrow C_6H_{12}O_6 + 6\ O_2 + 6\ H_2O \qquad \text{Equation 2}$$

Algae are thus able to convert the $CO_2$ absorbed by the absorbent liquid into glucose and oxygen. Glucose and oxygen can be used by the algae to produce energy and/or biomass. During the photosynthesis process, the absorbent liquid is regenerated and can be recovered. In a method of the invention, the regenerated absorbent liquid is reintroduced from the algae pond into the absorbing unit. Before the absorbent liquid is reintroduced into the absorbing unit, it is preferably combined with the liquid stream comprising the enzyme, which is reintroduced from the separation step into the absorbing unit. The two streams comprising the recycled enzyme, respectively the recovered absorbent liquid can, however, also be combined within the absorbing unit, or even thereafter, provided the two streams are combined upstream of the filtration unit.

In order for the enzyme, preferably carbonic anhydrase or an analogue thereof, to catalyse the conversion of $CO_2$ into soluble inorganic carbon, $CO_2$ must first be absorbed by the absorbent liquid. $CO_2$ absorbs spontaneously in aqueous solutions, although at low concentrations and absorption speed. Absorption speed and concentration of $CO_2$ in the absorbent liquid can, for instance, be increased by solvents capable of enhancing $CO_2$ absorption.

In a preferred embodiment, a method according to the invention is provided, wherein said absorbent liquid comprises a solvent capable of enhancing $CO_2$ absorption into said absorbent liquid. In a more preferred embodiment, said solvent comprises bicarbonate ($HCO_3^-$), carbonate ($CO_3^{2-}$), a primary or secondary or tertiary amine or an amino acid.

The catalytic conversion thus preferably results in an inorganic carbon which is more soluble in the absorbent liquid than $CO_2$. Even more preferred, the more soluble inorganic carbon comprises an $HCO_3^-$ and/or a $CO_3^{2-}$ anion. Such anions can be taken up by the algae and used for conversion into biomass and/or oxygen. In a preferred embodiment, therefore, a method according to the invention is provided, wherein said more soluble inorganic carbon comprises $HCO_3^-$ and/or $CO_3^{2-}$.

As described above, a method according to the invention involves separation of the liquid stream comprising both the enzyme used for conversion of $CO_2$ and the soluble inorganic carbon into two separate liquid streams. It is preferred that at least part of the enzyme is recycled, such that it is again available in the absorbent liquid stream when it is contacted with the $CO_2$ comprising gaseous stream. Because, in general, an enzyme is expensive, it is preferred that at least part of the enzyme is recycled. This is achieved by a means capable of separating the enzyme together with a portion of the absorbent liquid from the remainder of the absorbent liquid. Thus, instead of adding the solubilised inorganic carbon together with the enzyme to the algae, the enzyme is recycled to the absorbing unit in order to avoid losses due to inactivation or breakdown of the enzyme in the algal pond. Preferably at least 50% of the enzyme is separated from the remainder of said liquid stream and recycled. More preferably at least 60%, more preferably at least 70%, more preferably at least 80%, more preferably at least 85%, more preferably at least 90%, more preferably at least 95%, more preferably at least 97%, more preferably at least 99%, most preferably at least 99.9% is separated from the remainder of the absorbent liquid and recycled to be contacted with the gaseous stream comprising $CO_2$. It is preferred that the portion of the absorbent liquid which is separated together with the enzyme is relative smaller than the portion of the enzyme separated. In other words, the enzyme is present in a higher concentration in the portion of the absorbent liquid, relative to the concentration of enzyme in the remainder of the absorbent liquid. Thus, preferably less than 50%, more preferably less than 40%, more preferably less than 30%, more preferably less than 20%, more preferably less than 10%, most preferably less than 5% of the absorbent liquid is recycled together with the enzyme and is not led into the algae pond or bioreactor. The efficiency with which the enzyme is recycled can be expressed by a parameter called separation efficiency, wherein separation efficiency is herewith defined by Equation 3:

$$\text{Seperation efficiency} = \frac{100 - \% \text{ liquid}}{100 - \% \text{ enzyme}} \quad \text{Equation 3}$$

wherein % liquid is the percentage of liquid which is led into the recycling stream and % enzyme is the percentage of catalyst which is led into the recycling stream. Of course, 100–% liquid and 100–% enzyme are thus the percentage of liquid and the percentage of enzyme, respectively, led into the algae pond or reactor.

Thus, if 50% of the enzyme is recycled together with 50% of the absorbent liquid, separation efficiency is 100–50/100–50=1. If, however, only 10% of the liquid is recycled together with 80% of the enzyme, separation efficiency is 100–10/100–80=4.5. For efficient separation and recycling of the enzyme, said separation efficiency is preferably higher than 1, more preferably at least 2, more preferably at least 4, more preferably at least 10, more preferably at least 20, more preferably at least 40, most preferably at least 90. A separation efficiency of at least 90 can for instance be achieved when 10% or less of liquid is recycled together with at least 99% of enzyme (100–10/100–99=90). Separation efficiencies well beyond 500 can be achieved if the % enzyme that is recycled is more than 99.9%. Of course it is much preferred to recycle more than 99.9% of the enzyme as this largely prevents loss of enzyme during operation.

The skilled person is aware of methods of separating proteinaceous compounds in a liquid stream. A preferred method is the use of a filter, for instance a polymeric or ceramic membrane filter, which are efficient in separating proteinaceous molecules. Typically, an ultrafiltration membrane can be used to effectively recover the enzymes from the stream before feeding into the algae pond. However, by cross-linking the enzyme large Cross-Linked Enzyme Aggregates (CLEA) can be formed which can even be filtered off using micro-filtration membranes thus improving the recovery of the enzymes. In a preferred embodiment, the invention thus provides a method according to the invention, wherein separating the first liquid stream comprising both the enzyme and the soluble inorganic carbon into said second and said third liquid stream is performed by using a filter, preferably a polymeric or ceramic membrane filter.

It is useful to increase absorption of $CO_2$ into the absorbent liquid in order to increase the amount of $CO_2$ which can subsequently be catalytically converted into soluble inorganic carbon. As mentioned above, this can be achieved by adding solvents capable of dissolving $CO_2$ into the absorbent liquid. Another possibility is to decrease the pH of the absorbent liquid. When $CO_2$ is absorbed in water, it will reversibly form a weak acid, called carbonic acid, $H_2CO_3$. In water, carbonic acid is reversibly converted into a hydronium cation, $H_3O^+$, and the bicarbonate ion, $HCO_3^-$. A more alkaline absorption fluid shifts the equilibrium of the reactions to the more water soluble bicarbonate and away from the gaseous $CO_2$, thereby increasing the amount of $CO_2$ dissolved in the absorbent liquid. Increasing the alkalinity raises the total inorganic carbon in the water while maintaining the same partial pressure of carbon dioxide. One way of increasing alkalinity is to dissolve calcium carbonate or calcium oxide to form bicarbonate ions. Of course, other methods may be used to increase the absorption of $CO_2$ even more, such as increased contact time between the gaseous and the liquid stream, temperature optimization, increased gas pressure, etc.

In a preferred embodiment, a method according to the invention is provided, wherein the absorbent liquid has a pH of above 7.5, preferably a pH of above 8.0, more preferably a pH of above 8.5, more preferably a pH of above 9.0, more preferably a pH of above 9.5, most preferably a pH of above 10.0.

It is preferred that the algae which are exposed to said liquid are alkaline tolerant because, as said above, the absorbent liquid preferably has an alkaline pH. In a preferred embodiment, therefore, a method according to the invention is provided, wherein said algae tolerate a pH of above 8.0, preferably above 8.5, more preferably above 9.0, more preferably above 9.5, most preferably above 10.0. With the term "tolerate" is meant that the algae are at least not irreversibly damaged. Preferably, the algae do not deteriorate in said alkaline absorbent liquid. More preferably, the algae are able to thrive in an environment with a pH of above 8.0, preferably above 8.5, more preferably above 9.0, more preferably above 9.5, most preferably above 10.0. Preferred examples of algae which flourish at alkaline pH, i.e. a pH of above 8.0 or higher are *Spirulina platensis* or *Neochloris oleoabundans*. The skilled person is aware of the effect of alkaline pH on different algae species. Catalytic activity, especially that of enzymes, is also influenced by pH. The highest enzyme activity of carbonic anhydrase is for instance around 8.1 (Kiese et al., *Journal of Biological Chemistry* 1940, 132, 281-292). It is thus preferred that especially when carbonic anhydrase is used as a catalytic enzyme, the absorbent liquid, at the moment that $CO_2$ is contacted with the enzyme, has a pH of between 6.0 and 10.0, preferably a pH of between 7.0 and 9.0, more preferably a pH of between 7.5 and 8.5, most preferably a pH of about 8.1.

In a preferred embodiment, therefore, a method according to the invention is provided, wherein said algae are *Spirulina platensis* or *Neochloris oleoabundans*, preferably *Spirulina platensis*.

The method is very useful for combining both the capture and conversion of $CO_2$, and the production of algae. In order to be able to use the algae for other purposes, such as the production of biofuel, the algae are preferably harvested.

In a preferred embodiment, a method according to the invention is provided, the method further comprising the step of harvesting said algae from said algal culture. Harvesting of algae can be done by methods known in the art, for instance by filtration, or by centrifugal processes.

Furthermore, algal products, such as β-carotene, antioxidants and biofuels can be harvested from the algal culture. These products, when exo-secreted can easily be obtained from the algal supernatant, preferably directly from the pond. However, for some products, the algae must first be harvested and disrupted before the algal products become available.

For instance, the algae may be used for the production of bio-fuel. For this purpose, bio-fuel precursors are preferably extracted from the algae, after which bio-fuel can be produced by conventional methods.

In a preferred embodiment, a method according to the invention is provided, wherein the method further comprises the step of:
  extracting one or more bio-fuel precursors from said algae, preferably followed by the step of:
  preparing bio-fuel from said bio-fuel precursors.

Many algae known in the art comprise bio-fuel precursors in the form of lipids or free fatty acids. Preferred species for use in a method according to the invention are *Neochloris oleoabundans* and *Chlorella protothecoides*.

In a preferred embodiment, therefore, a method according to the invention is provided, wherein said algae are oleaginous algae, preferably *Neochloris oleoabundans* or *Chlorella protothecoides*.

As mentioned above, algae can be cultured in a closed bioreactor or in an open pond. Although both culturing environments are suitable for use in a method according to the invention, it is preferred to use an open pond as an open pond is less expensive. Different types of bioreactors or open ponds for culturing algae are well known to the skilled person. For instance, an open pond covered with a transparent or translucent barrier is very useful in a method according to the invention. It advantageously combines properties of an open pond with properties of a bioreactor by giving better control over the delivery of $CO_2$ into the systems. It is for instance less expensive than a closed bioreactor, it protects the algae from possible contamination and largely from temperature and weather influences, to which the algae are exposed in an open pond. Therefore, it can be used all year around, provided the pond is subjected to a source of heat. Especially when coupled to a coal-fired power plant, such covered open pond can be easily heated by subjecting the pond to (part of) the warmth of the flue gas.

In a preferred embodiment therefore, a method according to the invention is provided, wherein said algal culture is an algal culture in a closed bioreactor or in an open pond. In a preferred embodiment, the algae are cultured in an open pond. In a more preferred embodiment, the open pond is covered with a transparent or translucent barrier, for instance a construction made from glass (e.g. a "greenhouse") or a plastic tent. In a most preferred embodiment, the open pond is heated such that it can be used all year around.

As said before, the enzyme, preferably carbonic anhydrase, is filtered in order to recycle the enzyme to be contacted with the gaseous stream comprising $CO_2$ before the absorbent liquid enters the bioreactor or pond. To increase filtration efficacy and/or in order to use larger pore-size filters, it is preferred to cross-link single enzyme molecules, for instance the carbonic anhydrase enzymes. Such cross-linked enzymes are larger and are therefore less likely to pass through the filter, thereby enhancing the enzyme recycling efficacy in said method.

In a preferred embodiment, therefore, a method according to the invention is provided, wherein at least two enzyme molecules, preferably at least two carbonic anhydrase enzyme molecules, are linked to one another. More preferably at least three, more preferably at least four enzyme molecules are linked to one another.

Now that the invention provides a method for advantageously combining $CO_2$ capture and algal growth, the invention further provides an apparatus especially adapted for said purpose.

In one embodiment, the invention provides an apparatus for removing $CO_2$ from a gaseous stream the apparatus comprising:
  a first fluid circulation system for circulating an aqueous absorbent liquid comprising an enzyme, preferably carbonic anhydrase, said first fluid circulation system comprising
    an absorbing unit comprising an inner space, configured to receive a gaseous stream comprising $CO_2$ to interact with said aqueous absorbent liquid,
    downstream of the absorbing unit a filtration unit comprising a filter for recycling the enzyme and supplying the enzyme back, together with a portion of the aqueous absorbent liquid, through said first fluid circulation system to the absorbing unit, a second fluid circulation system substantially parallel to at least part of said first circulation system, at a first side extending from the filtration unit and at a second end extending from the first circulation system adjacent or at a short distance upstream of the absorbing unit, said second fluid circulation system being configured for transporting a remainder of the aqueous absorbent liquid back to the first fluid circulation system, preferably adjacent or at a short distance upstream of the absorbing unit, wherein said second fluid circulation system comprises a bioreactor for culturing microorganisms, preferably algae.

In a preferred embodiment, the apparatus according to the invention is used in a method according to the invention.

The apparatus preferably comprises
  a first fluid circulation system for circulating an $CO_2$ absorbent liquid, said first fluid circulation system comprising
    an absorbing unit 15 comprising an inner space 4, configured to receive a gaseous stream comprising $CO_2$ to interact with said $CO_2$ absorbent liquid,
    downstream of the absorbing unit 15 a filtration unit 8 comprising a filter 7 for recycling the enzyme and supplying the enzyme back, together with a portion of the aqueous absorbent liquid, through said first fluid circulation system to the absorbing unit 15,
  a second fluid circulation system substantially parallel to at least part of said first circulation system, at a first side extending from the filtration unit 8 and at a second end extending from the first circulation system adjacent or at a short distance upstream of the absorbing unit 15, said second fluid circulation system being configured for transporting a remainder of the aqueous absorbent liquid back to the first fluid circulation system, preferably adjacent or at a short distance upstream of the absorbing unit, wherein said second fluid circulation system comprises a bioreactor or pond 2 for culturing microorganisms, preferably algae.

For a typical configuration of an apparatus that can be used in a method according to the invention, reference is made to FIG. 1.

FIG. 1 shows an illustration of an apparatus according to the invention for integration of the capture of $CO_2$ with direct consumption/regeneration of the absorbent liquid with algae. Said apparatus comprises a first fluid circulation system 16 for circulating an aqueous absorbent liquid comprising an enzyme, preferably carbonic anhydrase capable of converting $CO_2$ into bicarbonate. Said first fluid circulation system comprises an absorbing unit 15. The absorbing unit 15, comprising an inner space 4, configured to receive a gaseous stream comprising $CO_2$ through a first inlet 1. When in use, it is for instance possible to lead exhaust flue gas from a power plant or a gaseous stream containing $CO_2$ into said absorbing unit through said first inlet 1. The inner space 4 is configured such that the gaseous stream entering the inner space 4 through said first inlet 1, is able to interact with an absorption liquid within said inner space. The inner space 4 of said absorbing unit 15 may for instance be equipped with a packed column absorber which is configured to operate in counter current mode with an opposing flow of the absorbent liquid. The absorbing unit is connected to said first fluid circulation system by a second inlet 14 and a second outlet 5. The second outlet 5 of said absorbing unit is configured such that it enables absorbent liquid to leave the inner space 4 of said absorbing unit 15. Said first fluid circulation system further comprises, downstream of the absorbing unit, a filtration unit 8, comprising a filter 7 for recycling the enzyme and supplying the enzyme back, together with a portion of the aqueous absorbent liquid, through said first fluid circulation system to the absorbing unit. For this purpose, the filter unit 8 is equipped with a first filter outlet 9. The apparatus of FIG. 1 further comprises a second fluid circulation system at a first side extending from the filtration unit 8, by second filtration outlet 10. Said second fluid circulation system is substantially parallel to at least part of said first circulation system and extends at a second end adjacent or at a short distance upstream of the absorbing unit of said first fluid circulation system. Said second fluid circulation system is configured such that it enables transporting of a remainder of the absorbent liquid back to the first fluid circulation unit into the absorbing unit 4.

The enzyme is thus recycled back to the absorbing unit in order to preserve the enzyme for further conversion of $CO_2$. However, even when the enzyme is recycled highly efficient, it is generally necessary to continuously add a small amount of enzyme in order to compensate for losses because of the filtration step or because of degradation of the enzyme itself. For this purpose, it is preferred that an inlet valve for adding the enzyme to the first circulation system is present in said apparatus, preferably upstream and adjacent to the absorbing unit 4. It is more preferred that such valve is automatically operated by a control for measuring the activity of the enzyme upstream of the valve. During operation, such control means measures the concentration or activity of the enzyme and, when said concentration or activity drops below a certain threshold, such control means opens said valve in order to provide a certain amount of enzyme to said first circulation system.

In a preferred embodiment, therefore, an apparatus according to the invention is provided wherein, upstream from the absorbing unit, an inlet valve is provided for adding the enzyme, preferably carbonic anhydrase to the first circulation system. In a more preferred embodiment, the apparatus comprises a control means for measuring the activity of the enzyme upstream of said valve and, if the activity or concentration of said enzyme reaches a certain threshold, adjusts said activity or concentration by adding more of the enzyme to said first circulation system through said valve.

During operation of said apparatus, a gaseous stream flowing from said first inlet 1 to set first outlet 3 is preferably operated in counter current mode with the absorption liquid stream flowing from said second inlet 14 to said second outlet 5 in opposing directions, allowing said gaseous stream to interact with said aqueous stream. Typically, during operation, a $CO_2$ rich gas stream is led into the absorbing unit through said first inlet 1 and a liquid capable of absorbing $CO_2$ is led into said second inlet 14, whereby the absorbing unit allows $CO_2$ to be absorbed from the gas stream into the liquid stream. Because of absorption of $CO_2$ from the gas stream into the liquid stream, the gas stream leaving the absorbing unit through said first outlet 3 comprises less $CO_2$ than the gas stream fed into said first inlet 1. The gaseous stream is thus reduced in $CO_2$ content as it passes the absorbing unit. In contrast, the absorbent liquid has taken up $CO_2$ and, therefore, the liquid stream leaving the absorbing unit through said second outlet 5 comprises more $CO_2$ than the liquid stream fed into the absorbing unit through said second inlet 14. When in use, typically, $CO_2$ leaving the absorbing unit in the absorption liquid through said second outlet 5 is in the form of bicarbonate, because an enzyme, preferably carbonic anhydrase, present in the absorbent liquid generally quickly catalyzes the conversion of $CO_2$ into bicarbonate.

The filtration unit 8 comprises a filtration inlet 6, a first filtration outlet 9, and a second filtration outlet 10, wherein a filter 7 is present between said filtration inlet 6 and said second filtration outlet 10. Preferably, no filter is present between said first filtration inlet 6 and said first filtration outlet 9. Said filtration unit 8 is configured such that, during operation, proteinaceous molecules are retained in the first circulation system, whereas non-proteinaceous molecules, such as carbonates, are able to escape said first circulation system, through said filter 7, into said second circulation system through second filtration outlet 10.

The second circulation system comprises a bioreactor or a pond 2 for culturing algae. During operation, the liquid stream leaving the filtration unit through second filtration outlet 10 is led into said bioreactor or pond 2 through pond inlet 11. The algae present in said bioreactor or pond are able to convert the $CO_2$ present in said liquid. Such conversion is illustrated by equation 2. During operation of the apparatus according to the invention, the absorbent liquid is thus regenerated in the algal bioreactor or pond 2, thereby promoting growth of the algae. The algal bioreactor or pond 2 is in fluid connection with the first circulation system, enabling during operation recycling of the regenerated absorbent liquid. The regenerated absorbent liquid is typically recombined with the recycled enzyme stream from the filtration unit 8. This combined stream is subsequently reintroduced into the absorbing unit 15 to be reused for capturing of $CO_2$ from the $CO_2$ rich gas stream.

The filter 7 used in an apparatus according to the invention can be any filter that enables, at least in part, the separation of the enzymes, from a liquid stream. Typically, nanofiltration, ultrafiltration and microfiltration membranes are used for the recovery of the proteinaceous molecules from solutions. Preferably, polymeric or ceramic membrane filters are used, because these kinds of filters are efficient for separation of proteinaceous molecules. In a preferred embodiment, therefore, an apparatus according to the invention is provided, wherein said filtration unit comprises a polymeric or ceramic membrane filter. These membranes can, for instance, be used in the spiral wound configuration or as hollow fibres.

An apparatus according to the invention for removing $CO_2$ from a gaseous stream, advantageously combines carbon capture and algal production. As explained above, typically, the land mass needed for algal ponds to remove $CO_2$ from a large coal-fired power plant restricts the use of algae in such process. However, using an apparatus according to the invention, smaller ponds can be placed beside coal-fired power plants to strip the flue gas of $CO_2$. Another advantage of the use of an apparatus according to the invention is the faster kinetics in the absorption of $CO_2$ from the exhaust gases due to the presence of the catalytic enzyme, preferably the enzyme carbonic anhydrase. Because the enzyme is at least partly recycled and preferably not fed into algal pond, loss of catalytic activity during the process is largely reduced. The use of carbonic anhydrase as a catalytic enzyme in the capture of $CO_2$ may result in an absorption of up to 90% of the gas from the exhaust stream.

Algae are categorised into microalgae and macroalgae. Although both algae may be used in the present invention, it is preferred to use microalgae (also referred to as phytoplankton, microphytes, or planktonic algae). Macroalgae, commonly known as seaweed, may also be used, but due to their size and the specific requirements of the environment in which they need to grow, are less preferred.

It is preferred that monocultural algae are used. With mixed cultures, one species may become dominant over time and may change the properties of the algal culture.

The water in the algal pond or bioreactor must be in a temperature range that will support the specific algal species being grown. Especially if the pond or bioreactor is to be used throughout the year, it is important to be able to regulate the temperature of the water. In case of stripping $CO_2$ from flue gas or the like, it is preferred to transfer (at least some of the) heat of the flue gas to the absorbent liquid, in order to warm up the pond or bioreactor to an acceptable temperature. It is, however, of importance to not warm up the absorbent liquid to a temperature higher than tolerated by the enzyme.

In order to convert $CO_2$ into oxygen and glucose, algae need light. Direct sunlight is too strong for most algae, which need only about $\frac{1}{10}$ of the amount of light they receive from direct sunlight. In a dense algal culture, light may only penetrate the top 3 to 4 inches (76-100 mm) of the water. When deeper ponds are used, the water should be agitated, such that the algae are circulated. This prevents both, over-exposure to sun-light and sedimentation of algae on the bottom of the pond which as a consequence thereof receive (almost) no light at all. Paddle wheels can stir the water and compressed air coming from the bottom may lift algae from the lower regions. Of course, the continuous stream of the absorbent liquid flowing into the pond or bioreactor can also be used to agitate the algae and is much preferred. Fluid jets may, for instance, be installed in the bottom of the pond which lift algae from the lower regions.

Another means of supplying light to the algae is for instance the use of glow plates made from sheets of plastic or glass and placed within the tank. Such glow plates are able to offer precise control over light intensity.

The use of algae is not necessarily restricted to the production of bio-fuel. Many uses are known in the art. The following examples should by no means be interpreted as restricting the invention in any way.

Several species of algae are raised for food. Purple layer (Porphyra), for instance is used in nori (Japan), gim (Korea), and laverbread (Wales).

Spirulina (*Arthrospira platensis*) is a blue-green microalgae high in protein and other nutrients and is used as a food supplement. *Chlorella*, is also used as a nutritional supplement with possible effects on metabolic rate. It has been reported that *Chlorella* can reduce mercury levels in humans.

Irish moss (*Chondrus crispus*), is a source of carrageenan, which can be used as a stiffening agent in instant puddings, sauces, and ice cream, or as a fining agent in beer.

Extracts and oils from algae can also be used as additives in various food products. Most plants produce Omega-3 and Omega-6 fatty acids, which have been shown to have positive health benefits.

Both microalgae and macroalgae can be used to make agar, which is an alternative to animal-derived gelatine.

Other possible uses of algae include the production of bioplastics, dyes, and pharmaceutical ingredients.

The following examples merely serve to explain the invention and do not limit the invention in any way.

EXAMPLE

Materials

2 M solution of sodium carbonate ($Na_2CO_3$) in water, carbonic anhydrase (lyophilised powder form) and pure $CO_2$ gas.

Methods

Using the 2 M solution of sodium carbonate ($Na_2CO_3$) in water, the rate of $CO_2$ uptake was measured. 50 ml of the solution was placed in a reactor cell and pulses of 0.045 l of $CO_2$ was injected in intervals into the liquid at constant temperature of 40° C. with the pressure monitored in time. For the reference case, no enzyme (carbonic anhydrase) was added to the solution. The catalysed solution contained 400 mg/l of enzyme. The two experiments were carried out under similar experimental conditions.

Figure 2:
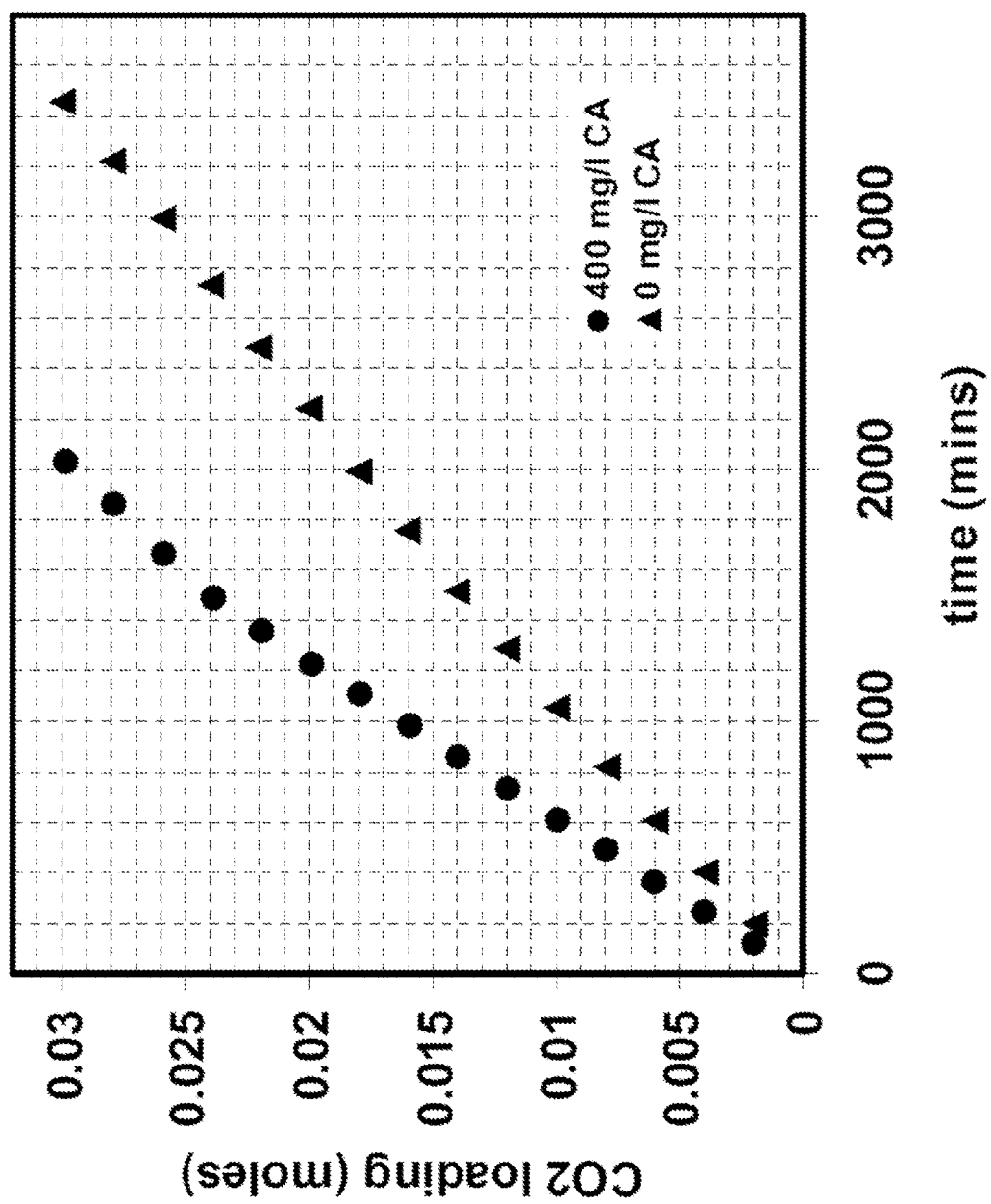
FIG. 2: Kinetic experiments showing the rate of $CO_2$ loading in the reference and catalysed tests.

By comparing the rate of uptake of $CO_2$ between the reference and enzyme catalysed experiments, it was observed that the rate of absorption in the presence of the enzyme was increased substantially by up to twofold (FIG. 2). FIG. 2 compares the two experiments (with and without carbonic anhydrase). It can be seen that the $CO_2$ capture rate in the catalysed system increases faster than without the enzyme.

The loaded solvent (sodium bicarbonate) was inoculated with algae (inoculum—0.23 g/l dry weight). After two weeks of growth, the algae were filtered off and the regenerated solvent was used in the absorbent step to re-capture $CO_2$, thereby closing the loop.

The invention claimed is:

1. A method for decreasing the amount of carbon dioxide ($CO_2$) in a gaseous stream, the method comprising the steps of
   a) contacting a gaseous stream comprising $CO_2$, with a first absorbent liquid stream comprising an enzyme capable of converting liquid-absorbed $CO_2$ into a more liquid-soluble inorganic carbon, wherein said enzyme is a carbonic anhydrase of class EC 4.2.1.1,
   b) allowing the $CO_2$ to be absorbed by said first absorbent liquid and allowing the liquid-absorbed $CO_2$ to be converted into said more soluble inorganic carbon,
   c) separating the first liquid stream into a second and a third liquid stream, each comprising both the enzyme and the dissolved inorganic carbon along with a portion of liquid absorbent from the first absorbent liquid stream, wherein
   d) said second liquid stream comprises, relative to said third liquid stream, a higher concentration of the enzyme,
   e) recycling said enzyme by supplying the enzyme in said second liquid stream back, together with the portion of the absorbent liquid, to be contacted with the gaseous stream in step a),
   f) contacting said third liquid stream with a microorganism capable of converting liquid-solubilised inorganic carbon into oxygen or biomass, wherein said microorganism is an algae tolerating a pH of above 8.0 in an algal culture,
   g) allowing the conversion of the liquid-soluble inorganic carbon by said microorganism, thereby regenerating the absorbent liquid,
   h) recycling the regenerated absorbent liquid to be contacted with the gaseous stream in step a).

2. The method according to claim 1, wherein said absorbent liquid comprises a solvent capable of enhancing $CO_2$ absorption into said absorbent liquid.

3. The method according to claim 2, wherein said solvent comprises bicarbonate ($HCO_3^-$), carbonate ($CO_3^{2-}$), a primary or secondary or tertiary amine, or an amino acid.

4. The method according to claim 1, wherein said more soluble inorganic carbon comprises a member of the group consisting of $HCO_3^-$, $CO_3^{2-}$, and mixtures thereof.

5. The method according to claim 1, wherein in step c) said first liquid stream is separated into said second and said third liquid stream by use of a filter.

6. The method according to claim 5, wherein said filter is a polymeric or ceramic membrane filter.

7. The method according to claim 1, wherein said absorbent liquid has a pH of above 8.0.

8. The method according to claim 1, the method further comprising the step of:
   i) harvesting said algae from said algal culture.

9. The method according to claim 8, the method further comprising the step of:
   j) extracting one or more bio-fuel precursors from said algae.

10. The method of claim 9, the method further comprising the step of:
    k) preparing bio-fuel from said bio-fuel precursors.

11. The method according to claim 1, wherein said algae are oleaginous algae.

12. The method according to claim 1, wherein said algal culture is in a closed bioreactor or in an open pond.

13. The method according to claim 12, wherein said algal culture is disposed in an open pond.

14. The method according to claim 1, wherein said carbonic anhydrase comprises at least two carbonic anhydrase molecules cross-linked to each other.

15. The method according to claim 1, wherein said algae are *Spirulina platensis* or *Neochloris oleoabundans*.

16. The method according to claim 1, wherein said algae are *Neochloris oleoabundans*.

17. An apparatus for removing $CO_2$ from a gaseous stream, comprising:
    a first fluid circulation system for circulating an aqueous absorbent liquid comprising an enzyme being carbonic anhydrase of class EC 4.2.1.1, said first fluid circulation system comprising
    an absorbing unit comprising an inner space, configured to receive a gaseous stream comprising $CO_2$ to interact with said aqueous absorbent liquid, and
    downstream of the absorbing unit a filtration unit comprising a filter configured to separate the enzyme for recycling the enzyme and supplying the enzyme back, together with a portion of the aqueous absorbent liquid, through said first fluid circulation system to the absorbing unit; and
    a second fluid circulation system substantially parallel to at least part of said first circulation system, at a first side extending from the filtration unit and at a second end extending from the first circulation system upstream of the absorbing unit and downstream of the filter unit, said second fluid circulation system comprises a bioreactor or pond for culturing microorganisms, wherein said microorganisms are an algae tolerating a pH of above 8.0 in an algal culture and wherein said second circulation system is configured for transporting a remainder of the aqueous absorbent liquid back to the first fluid circulation system.

18. The apparatus according to claim 17, wherein, upstream from the absorbing unit, an inlet valve is provided for adding the enzyme to the first circulation system, wherein the apparatus comprises a control for measuring the activity of the enzyme upstream of the valve.

19. The apparatus according to claim 17, wherein said second fluid circulation system comprises
 a) a bioreactor or pond for said algae or
 b) is configured for transporting a remainder of the aqueous absorbent liquid back to the first fluid circulation system adjacent or at a short distance upstream of the absorbing unit.

* * * * *